United States Patent
Lei et al.

(10) Patent No.: US 9,856,192 B2
(45) Date of Patent: Jan. 2, 2018

(54) METHOD FOR PREPARING 2,3,3,3-TETRAFLUOROPROPENE AND 1,3,3,3-TETRAFLUOROPROPENE

(71) Applicants: Zhejiang Quzhou Juxin Fluorine Chemical Co., Ltd., Quzhou (CN); Zhejiang Quhua Fluor-Chemistry Co., Ltd., Quzhou (CN)

(72) Inventors: Jun Lei, Ningbo (CN); Aiguo Wang, Quzhou (CN); Bo Yang, Quzhou (CN); Yan Zhang, Quzhou (CN); Huadong Zhou, Quzhou (CN); Yang Zhao, Quzhou (CN); Guoan Liu, Quzhou (CN); Yi Zhu, Quzhou (CN); Gang Su, Quzhou (CN)

(73) Assignees: ZHEJIANG QUZHOU JUXIN FLUORINE CHEMICAL CO., LTD., Quzhou (CN); ZHEJIANG QUHUA FLUOR-CHEMISTRY CO., LTD., Quzhou (CN)

( * ) Notice: Subject to any disclaimer, the term of this patent is extended or adjusted under 35 U.S.C. 154(b) by 0 days.

(21) Appl. No.: 15/405,268

(22) Filed: Jan. 12, 2017

(65) Prior Publication Data
US 2017/0144950 A1 May 25, 2017

Related U.S. Application Data

(63) Continuation-in-part of application No. PCT/CN2015/000654, filed on Sep. 21, 2015.

(30) Foreign Application Priority Data

Jun. 11, 2015 (CN) .......................... 2015 1 0321156

(51) Int. Cl.
*C07C 17/25* (2006.01)
*C07C 17/354* (2006.01)
(Continued)

(52) U.S. Cl.
CPC ............ *C07C 17/25* (2013.01); *C07C 17/354* (2013.01); *C07C 17/38* (2013.01); *C07C 17/383* (2013.01)

(58) Field of Classification Search
CPC ........ C07C 17/23; C07C 17/354; C07C 17/25
See application file for complete search history.

(56) References Cited

U.S. PATENT DOCUMENTS

| | | | |
|---|---|---|---|
| 7,902,410 B2 * | 3/2011 | Van Der Puy | ........ C07C 17/354 570/175 |
| 8,420,873 B2 * | 4/2013 | Takahashi | ............... C07C 17/25 570/155 |

(Continued)

*Primary Examiner* — Medhanit W Bahta
(74) *Attorney, Agent, or Firm* — Matthias Scholl, PC; Matthias Scholl (57) ABSTRACT

A method for preparing 2,3,3,3-tetrafluoropropene and 1,3,3,3-tetrafluoropropene, including: providing a first reactor including a first section, a second section, and a third section, with each section being filled with different catalysts, preheating hexafluoropropylene and hydrogen, and introducing the hexafluoropropylene and the hydrogen to the first reactor to yield a first mixture including: 1,1,1,2,3-pentafluoropropane, 1,1,1,2,3,3-hexafluoropropane, and hydrogen fluoride; introducing the first mixture to a first distillation column to yield 1,1,1,2,3,3-hexafluoropropane at a top of the first distillation column and 1,1,1,2,3-pentafluoropropane and hydrogen fluoride at a bottom of the first distillation column, recycling the 1,1,1,2,3,3-hexafluoropropane to a lower part of the first section of the first reactor, and introducing the 1,1,1,2,3-pentafluoropropane and the hydrogen fluoride to a second reactor to yield a second mixture including: 2,3,3,3-tetrafluoropropene, 1,3,3,3-tetrafluoropropene, hydrogen fluoride, and 1,1,1,2,3-pentafluoropropane; and performing water washing, alkaline washing, drying, and distillation on the second mixture to yield 2,3,3,3-tetrafluoropropene and 1,3,3,3-tetrafluoropropene.

3 Claims, 1 Drawing Sheet

(51) Int. Cl.
*C07C 17/383* (2006.01)
*C07C 17/38* (2006.01)

(56) References Cited

U.S. PATENT DOCUMENTS

| | | | | |
|---|---|---|---|---|
| 8,471,078 B2* | 6/2013 | Low | ........................ | C07C 17/23 570/123 |
| 2013/0006022 A1* | 1/2013 | Shiotani | .................. | C07C 17/23 570/175 |

* cited by examiner

METHOD FOR PREPARING 2,3,3,3-TETRAFLUOROPROPENE AND 1,3,3,3-TETRAFLUOROPROPENE

CROSS-REFERENCE TO RELATED APPLICATIONS

This application is a continuation-in-part of International Patent Application No. PCT/CN2015/000654 with an international filing date of Sep. 21, 2015, designating the United States, now pending, and further claims foreign priority benefits to Chinese Patent Application No. 201510321156.4 filed Jun. 11, 2015. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a method for preparing 2,3,3,3-tetrafluoropropene and 1,3,3,3-tetrafluoropropene.

Description of the Related Art

Conventionally, 1,3,3,3-tetrafluoropropene is prepared by dehydrofluorination of 1,1,1,3,3-pentafluoropropane. However, the 1,1,1,3,3-pentafluoropropane is relatively expensive.

Conventionally, 2,3,3,3-tetrafluoropropene is prepared using hexafluoropropylene and hydrogen as raw materials by a two-step hydrogenation and a two-step dehydrofluorination. However, such a method is complex, costly, energy-consuming, and inefficient.

SUMMARY OF THE INVENTION

In view of the above-described problems, it is one objective of the invention to provide an improved method for preparing 2,3,3,3-tetrafluoropropene and 1,3,3,3-tetrafluoropropene.

To achieve the above objective, in accordance with one embodiment of the invention, there is provided a method for preparing 2,3,3,3-tetrafluoropropene and 1,3,3,3-tetrafluoropropene. The method comprises:

a) providing a first reactor comprising a first section, a second section, and a third section, and loading a first catalyst, a second catalyst, and a third catalyst respectively to the first section, the second section, and the third section of the first reactor; preheating hexafluoropropylene and hydrogen, and introducing the hexafluoropropylene and the hydrogen to the first reactor to carry out reactions in the first section, the second section, and the third section respectively so as to yield a first mixture comprising: 1,1,1,2,3-pentafluoropropane, 1,1,1,2,3-hexafluoropropane, and hydrogen fluoride, in which a molar ratio of the hexafluoropropylene to the hydrogen is between 2:1 and 5:1 and a space velocity of the hexafluoropropylene and the hydrogen is between 100 and 1000 $h^{-1}$, a reaction temperature in the first section is between 50 and 200° C., a reaction temperature in the second section is between 150 and 300° C., and a temperature in the third section is maintained by materials from the second section;

b) introducing the first mixture obtained from a) to a first distillation column to yield 1,1,1,2,3,3-hexafluoropropane at a top of the first distillation column and 1,1,1,2,3-pentafluoropropane and hydrogen fluoride at a bottom of the first distillation column; recycling the 1,1,1,2,3,3-hexafluoropropane to a lower part of the first section of the first reactor; introducing the 1,1,1,2,3-pentafluoropropane and the hydrogen fluoride to a second reactor to allow the 1,1,1,2,3-pentafluoropropane to react with the hydrogen fluoride in the presence of a fourth catalyst at a reaction temperature of between 200 and 450° C. to yield a second mixture comprising: 2,3,3,3-tetrafluoropropene, 1,3,3,3-tetrafluoropropene, hydrogen fluoride, and 1,1,1,2,3-pentafluoropropane;

c) washing the second mixture obtained in b) using water and an alkali respectively, drying a treated second mixture to yield a third mixture comprising: 2,3,3,3-tetrafluoropropene, 1,3,3,3-tetrafluoropropene, and 1,1,1,2,3-pentafluoropropane; introducing the third mixture into a second distillation column to yield the 2,3,3,3-tetrafluoropropene and the 1,3,3,3-tetrafluoropropene at a top of the second distillation column and the 1,1,1,2,3-pentafluoropropane at a bottom of the second distillation column; and recycling the 1,1,1,2,3-pentafluoropropane to the second reactor; and d) introducing the 2,3,3,3-tetrafluoropropene and the 1,3,3,3-tetrafluoropropene obtained from c) into a third distillation column to yield the 2,3,3,3-tetrafluoropropene at a top of the third distillation column and the 1,3,3,3-tetrafluoropropene at a bottom of the third distillation column.

In a class of this embodiment, a molar ratio of hydrogen to hexafluoropropylene in a) is between 2:1 and 2.5:1, and the space velocity is between 200 and 800 $h^{-1}$. The reaction temperature in the first section is between 55 and 150° C., and the reaction temperature in the second section is between 180 and 250° C.

In a class of this embodiment, the reaction temperature of the second reactor in b) is between 250 and 400° C.

In a class of this embodiment, in a), the first catalyst in the first section of the first reactor is $Pd/Al_2O_3$, and Pd accounts for between 0.3 and 3 wt. %.

In a class of this embodiment, in a), the second catalyst in the second section of the first reactor comprises: between 5 and 10 wt. % of chromium oxide, between 80 and 90 wt. % of alumina, and between 3 and 10 wt. % of zinc oxide.

In a class of this embodiment, in a), the third catalyst in the third section of the first reactor is $Pd/AlF_3$ or Pd/C, and Pd accounts for between 0.3 and 3 wt. %.

In a class of this embodiment, the fourth catalyst of b) comprises: between 60 and 80 wt. % of chromium oxide, between 4 and 10 wt. % of indium oxide, and between 10 and 35 wt. % of nickel oxide.

The first reactor is divided into the first section, the second section, and the third section; and each section is filled with different catalyst. Raw materials of hexafluoropropylene and $H_2$ after being preheated by the preheater enter the first reactor to carry out reactions respectively in the first section, the second section, and the third section. In the first section, hexafluoropropylene is totally converted and a mixture comprising 1,1,1,2,3,3-hexafluoropropane and $H_2$ is yielded. The mixture comprising 1,1,1,2,3,3-hexafluoropropane and $H_2$ is introduced to the second section for dehydrofluorinating 1,1,1,2,3,3-hexafluoropropane and then to a third section for hydrogenation so as to yield a first mixture comprising 1,1,1,2,3-pentafluoropropane, 1,1,1,2,3,3-hexafluoropropane, HF, and $H_2$.

Hydrogenation of hexafluoropropylene is carried out in the first section of the first reactor. The reaction is a strong exothermic reaction. The reaction temperature has great influence on the catalytic activity and the selectivity of the products. The increase of the reaction temperature is beneficial to improve the catalytic activity. However, because the hydrogenation of the hexafluoropropylene is easily carried out, the conversion of hexafluoropropylene and the selectivity of FC-236ea may reach 100% at relatively low temperature. Considering the industrial application value of the catalyst, the reaction temperature must be decreased as much as possible on the premise of ensuring the high catalytic activity so as to reduce the energy consumption. Thus, the temperature of the first section is controlled between 50 and 200° C., and preferably between 55 and 150° C. With the increase of the space velocity, the contact time between the reactants and the catalyst bed is shortened, and the catalytic activity is reduced. To ensure total conversion of hexafluoropropylene, the space velocity is between 100 and 1000 $h^{-1}$, and preferably between 200 and 800 $h^{-1}$. The reaction is greatly affected by the molar ratio of $H_2$ to hexafluoropropylene. The lower the molar ratio is, the lower the concentration of $H_2$ in the reaction system is, and the lower the catalytic activity is. While the increase of the molar ratio of $H_2$ to hexafluoropropylene is able to effectively prevent the catalyst from coking and to improve the selectivity and stability of the catalyst so as to gradually improve the catalytic activity. Because the overdose of the hydrogen is able to carry the heat quantity of the reaction and to provide raw materials for the hydrogenation of the third section, the molar ratio of the hydrogen to the hexafluoropropylene is controlled between 2:1 and 5:1, and preferably between 2:1 and 2.5:1.

Dehydrofluorination is carried out in the second section in gas phase, in which, the temperature is high, the conversion of 1,1,1,2,3,3-hexafluoropropane is high, but the selectivity of the target product is low. According to the performance of the catalyst and the demonstration of the conversion and selectivity, the reaction temperature is selected between 150 and 300° C., and preferably between 180 and 250° C.

The third section of the first reactor does not require heating from the external. The materials from the second section directly enters the third section to make the temperature of the third section satisfy the reaction temperature, thus, the comprehensive utilization of the heat quantity is realized, and the energy consumption is decreased.

In condition of too low the reaction temperature in the second reactor, the single pass conversion of 1,1,1,2,3-pentafluoropropane is low, and the reaction is carried out towards the direction of the formation of 1,3,3,3-tetrafluoropropene; and in condition of high temperature in the second reactor, the reaction is carried out towards the direction of the formation of 2,3,3,3-tetrafluoropropene. The reaction temperature of the second reactor can be regulated according to the requirement of the products.

Comprehensively considering the conversion and the product components, the reaction temperature in the second reactor is between 200 and 450° C., and preferably between 250 and 400° C.

The first section and the third section of the first reactor are filled with catalyst comprising the noble metal Pd. When preparing the loaded type noble metal catalyst, the content of the Pd as the active component has great influence on the performance of the catalyst. Too small the load of Pd leads to insufficient catalytic activity; and too high the load make the prepared catalyst easily deactivated. In a certain range, the conversion of the catalyst increases with the increase in the load of Pd as the active component, but the higher the load of the Pd does not always results in the higher the conversion. In fact, a balanced value exists in the content of Pd, the dispersion state of Pd has close relation with the catalytic activity, but when the content of Pd infinitively increases, the variation in the dispersion degree of Pd is not obvious. When the load of Pd increases, the selectivity of the main product may correspondingly decrease. Thus, considering from the economic and experimental requirements, the best load of the catalyst must decrease as much as possible on the premise of ensuring high conversion and selectivity of the products.

Primary reasons for the deactivation of the catalyst Pd include: drainage of Pd, sintering of Pd, coking and carbonization, and catalyst poisoning. When the water content in the raw gas is too high, the drainage of Pd as the active component of the catalyst is resulted. When the temperature is high, the specific area of the catalyst and the number of the micropores are reduced, Pd as the active component is loaded in the channel of the carrier, the micropores are partially filled so that the number and the volume of the micropores are reduced. The high temperature may also result in the sintering of the Pd particles. Impurities, such as arsenic, sulfur, and carbon monoxide in the raw materials also lead to the catalyst poisoning.

Catalysts adopting chromium oxide as the active component known in the technical field are employed in the second section of the first reactor and the second reactor. The second catalyst in the second section of the first reactor preferably comprises: between 5 and 10 wt. % of chromium oxide, between 80 and 90 wt. % of alumina, and between 3 and 10 wt. % of zinc oxide, and is prepared by impregnating the chlorides of chromium and zinc onto alumina as a carrier, drying and calcining resulting products to make the chlorides of chromium and zinc oxidized, and fluoridating the oxides of chromium and zinc to yield the second catalyst. The fourth catalyst in the second reactor preferably comprises: between 60 and 80 wt. % of chromium oxide, between 4 and 10 wt. % of indium oxide, and between 10 and 35 wt. % of nickel oxide, and is prepared by allowing chlorides of chromium, indium, and nickel to react with a precipitant to yield hydroxides in a state of suspended solids, filtering, washing, drying, and calcining the hydroxides to yield oxides of chromium, indium, and nickel, granulating and tableting the oxides of chromium, indium, and nickel to yield a catalyst precursor, and fluoridating the catalyst precursor to yield the fourth catalyst. The activation of the catalyst can be performed in other reactors.

The first reactor and the second reactor can adopt the isothermal type or the adiabatic type. The reactors are made of materials that are acid corrosion resistant, such as Inconel. Plate comprising holes are arranged between adjacent sections of the first reactor, and the catalysts are filled from the bottom upwards according to the third section, the second section, and the first section. The appearance of the catalyst preferably adopts the sphere or cylinder so as to maintain the smooth gas velocity, ensure the uniform porosity, and prevent the gas mixture from dispersion in the axial and radial directions.

Advantages of the method for preparing 2,3,3,3-tetrafluoropropene and 1,3,3,3-tetrafluoropropene according to embodiments of the invention are summarized as follows:
1. The first reactor is filled with three different catalysts for carrying out three reactions respectively thus simplifying the process flow.
2. By adjusting the molar ratio of hydrogen to hexafluoropropylene in the reactor and optimizing parameters including the catalysts, the reaction temperature, and the space velocity, conversion of the hexafluoropropylene reaches 100%.
3. The third section of the first reactor does not require heating from the external. Materials from the second section directly enter the third section to sustain the required reaction temperature in the third section, so that the comprehensive utilization of the heat quantity is realized and the energy consumption is reduced.
4. The reaction system is able to prepare 2,3,3,3-tetrafluoropropene and 1,3,3,3-tetrafluoropropene as two products at the same time, and the products ratio can be flexibly adjusted according to the market demands, thus, the investment cost of the device is significantly reduced.

BRIEF DESCRIPTION OF THE DRAWINGS

The invention is described hereinbelow with reference to accompanying drawings, in which the sole FIGURE is a flow chart of a method for preparing 2,3,3,3-tetrafluoropropene and 1,3,3,3-tetrafluoropropene according to one embodiment of the invention.

In the drawing, the following reference numbers are used: 1. Preheater; 2. First reactor; 3. First distillation column; 4. Second reactor; 5. Water washing column; 6. Alkaline washing column; 7. Drying column; 8. Second distillation column; 9. Third distillation column; and 10-23. Pipelines.

DETAILED DESCRIPTION OF THE EMBODIMENTS

For further illustrating the invention, experiments detailing a method for preparing 2,3,3,3-tetrafluoropropene and 1,3,3,3-tetrafluoropropene are described below. It should be noted that the following examples are intended to describe and not to limit the invention.

Figure 1:
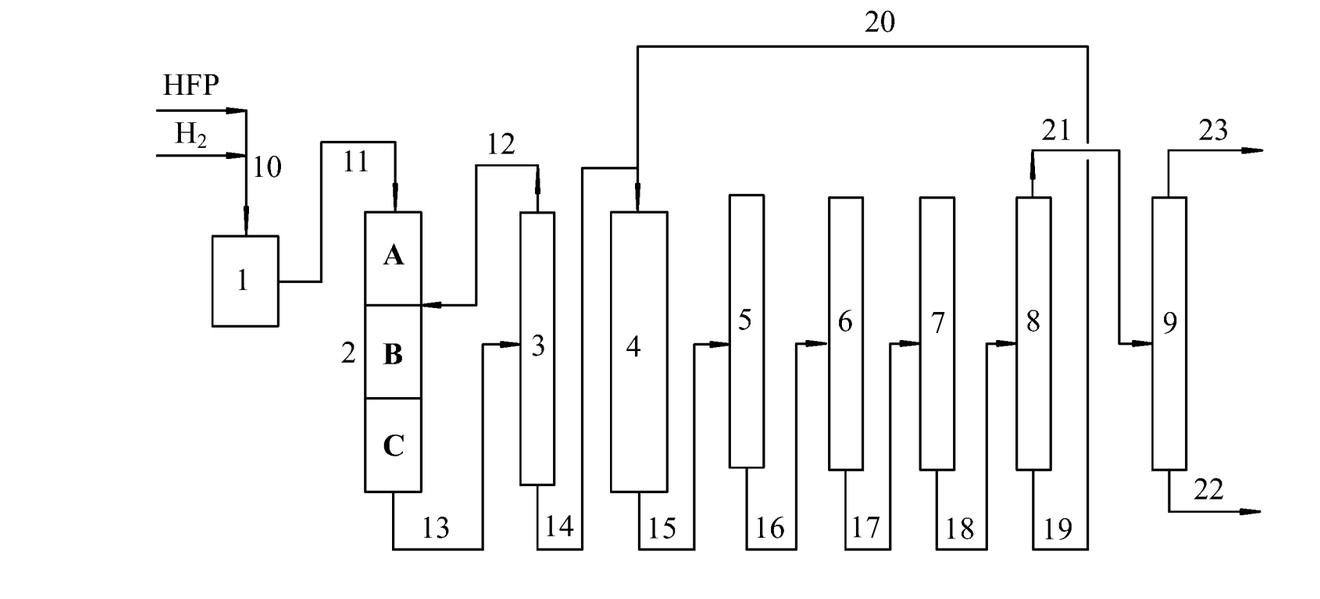

As shown in the sole FIGURE, the first reactor 2 is divided into the first section, the second section, and the third section, and each section is filled with different catalysts. Hexafluoropropylene and $H_2$ as raw materials are introduced via a pipeline 10 into a preheater 1 for preheating, and then introduced via a pipeline 11 to a first reactor 2 for carrying out reactions respectively in the first section, the second section, and the third section. In the first section, hexafluoropropylene is totally converted and a mixture comprising 1,1,1,2,3,3-hexafluoropropane and $H_2$ is yielded. The mixture comprising 1,1,1,2,3,3-hexafluoropropane and $H_2$ is introduced to the second section for dehydrofluorinating 1,1,1,2,3,3-hexafluoropropane and then to a third section for hydrogenation so as to yield a first mixture comprising 1,1,1,2,3-pentafluoropropane, 1,1,1,2,3,3-hexafluoropropane, HF, and $H_2$. The first mixture is introduced via a pipeline 13 to a first distillation column 3 to separate 1,1,1,2,3,3-hexafluoropropane at a top of the first distillation column 3 and 1,1,1,2,3-pentafluoropropane and HF at a bottom of the first distillation column 3. The separated 1,1,1,2,3,3-hexafluoropropane is returned to a lower part of the first section of the first reactor via a pipeline 12 and the separated 1,1,1,2,3-pentafluoropropane and HF are introduced to a second reactor 4 via a pipeline 14. And a small amount of $H_2$ in the first distillation is discharged as a non-condensed gas. A second mixture comprising: 2,3,3,3-tetrafluoropropene, 1,3,3,3-tetrafluoropropene, HF, and non-reacted 1,1,1,2,3-pentafluoropropane was discharged from the second reactor 4 via an outlet. The second mixture then introduced via a pipeline 15 to a water washing column 5 for removing HF, into an alkaline washing column 6 via a pipeline 16 for further removing residual HF, and then into a drying column 7 via a pipeline 17 for removing water to yield a third mixture comprising: 2,3,3,3-tetrafluoropropene, 1,3,3,3-tetrafluoropropene, and 1,1,1,2,3-pentafluoropropane. The third mixture is introduced into a second distillation column 8 via a pipeline 18 to yield 1,1,1,2,3-pentafluoropropane at a bottom of the second distillation column and to yield 2,3,3,3-tetrafluoropropene and 1,3,3,3-tetrafluoropropene at a top of the second distillation column. The 1,1,1,2,3-pentafluoropropane is recycled to the second reactor for reaction via pipelines 19, 20. The 2,3,3,3-tetrafluoropropene and the 1,3,3,3-tetrafluoropropene are introduced via a pipeline 21 to a third distillation column to yield 2,3,3,3-tetrafluoropropene at a top of the third distillation column and to yield 1,3,3,3-tetrafluoropropene at a bottom of the third distillation column. The 2,3,3,3-tetrafluoropropene is discharged via a pipeline 23 and packed, and the 1,3,3,3-tetrafluoropropene is discharged via a pipeline 22 and packed.

EXAMPLE 1

200 mL of $Pd/AlF_3$ as a third catalyst (Pd accounts for 0.3 wt. %) was added to a third section of a first reactor, 300 mL of a second catalyst comprising 5 wt. % of chromium oxide, 90 wt. % of alumina, and 5 wt. % of zinc oxide was added to a second section of the first reactor, and 200 mL of $Pd/Al_2O_3$ as a first catalyst (Pd accounts for 0.3 wt. %) was added to a first section of the first reactor. 700 mL of a fourth catalyst comprising 60 wt. % of chromium oxide, 5 wt. % of indium oxide, and 35 wt. % of nickel oxide was added to a second reactor.

The first section of the first reactor was heated to 55° C., the second section of the first reactor was heated to 200° C., and the second reactor was heated to 300° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H2 were mixed and introduced to a preheater, in which a molar ratio of hexafluoropropylene to H2 was 2:1 and a space velocity was 300 h−1. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 1:

TABLE 1

| Components | 2,3,3,3-tetra-fluoropropene | 1,3,3,3-tetra-fluoropropene | 1,1,1,2,3,3-hexa-fluoropropane | 1,1,1,2,3-pentafluoro-propane | Others |
|---|---|---|---|---|---|
| First reactor (wt. %) | 0.1 | 0.05 | 53.4 | 46.25 | 0.2 |
| Second reactor (wt. %) | 60.3 | 39.2 | 0 | 0.3 | 0.2 |

EXAMPLE 2

200 mL of Pd/AlF$_3$ as a third catalyst (Pd accounts for 0.6 wt. %) was added to a third section of a first reactor, 300 mL of a second catalyst comprising 10 wt. % of chromium oxide, 80 wt. % of alumina, and 10 wt. % of zinc oxide was added to a second section of the first reactor, and 200 mL of Pd/Al$_2$O$_3$ as a first catalyst (Pd accounts for 1 wt. %) was added to a first section of the first reactor. 700 mL of a fourth catalyst comprising 80 wt. % of chromium oxide, 10 wt. % of indium oxide, and 10 wt. % of nickel oxide was added to a second reactor.

The first section of the first reactor was heated to 70° C., the second section of the first reactor was heated to 240° C., and the second reactor was heated to 330° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H2 were mixed and introduced to a preheater, in which a molar ratio of hexafluoropropylene to H2 was 2.5:1 and a space velocity was 500 h−1. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 2:

TABLE 2

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.2 | 0.2 | 48.5 | 50.8 | 0.3 |
| Second reactor (wt. %) | 65.1 | 34.6 | 0 | 0.2 | 0.1 |

EXAMPLE 3

200 mL of Pd/C as a third catalyst (Pd accounts for 0.3 wt. %) was added to a third section of a first reactor, 300 mL of a second catalyst comprising 8 wt. % of chromium oxide, 85 wt. % of alumina, and 7 wt. % of zinc oxide was added to a second section of the first reactor, and 200 mL of Pd/Al$_2$O$_3$ as a first catalyst (Pd accounts for 1.5 wt. %) was added to a first section of the first reactor. 700 mL of a fourth catalyst comprising 66 wt. % of chromium oxide, 7 wt. % of indium oxide, and 27 wt. % of nickel oxide was added to a second reactor.

The first section of the first reactor was heated to 65° C., the second section of the first reactor was heated to 250° C., and the second reactor was heated to 350° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H$_2$ were mixed and introduced to a preheater, in which a molar ratio of hexafluoropropylene to H$_2$ was 3:1 and a space velocity was 800 h$^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 3:

TABLE 3

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.1 | 0 | 66.8 | 32.6 | 0.5 |
| Second reactor (wt. %) | 69.2 | 30.3 | 0 | 0.1 | 0.4 |

EXAMPLE 4

200 mL of Pd/C as a third catalyst (Pd accounts for 1 wt. %) was added to a third section of a first reactor, 300 mL of a second catalyst comprising 6 wt. % of chromium oxide, 90 wt. % of alumina, and 4 wt. % of zinc oxide was added to a second section of the first reactor, and 200 mL of Pd/Al$_2$O$_3$ as a first catalyst (Pd accounts for 3 wt. %) was added to a first section of the first reactor. 700 mL of a fourth catalyst comprising 70 wt. % of chromium oxide, 8 wt. % of indium oxide, and 22 wt. % of nickel oxide was added to a second reactor.

The first section of the first reactor was heated to 100° C., the second section of the first reactor was heated to 210° C., and the second reactor was heated to 280° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H$_2$ were mixed and introduced to a preheater, in which a molar ratio of hexafluoropropylene to H$_2$ was 2.5:1 and a space velocity was 200 h$^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 4:

TABLE 4

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.1 | 0 | 45 | 54.8 | 0.1 |
| Second reactor (wt. %) | 62.8 | 36.6 | 0.1 | 0.2 | 0.3 |

EXAMPLE 5

200 mL of Pd/C as a third catalyst (Pd accounts for 0.5 wt. %) was added to a third section of a first reactor, 300 mL of a second catalyst comprising 5 wt. % of chromium oxide, 85 wt. % of alumina, and 10 wt. % of zinc oxide was added to a second section of the first reactor, and 200 mL of Pd/Al$_2$O$_3$ as a first catalyst (Pd accounts for 0.8 wt. %) was added to a first section of the first reactor. 700 mL of a fourth catalyst comprising 75 wt. % of chromium oxide, 5 wt. % of indium oxide, and 20 wt. % of nickel oxide was added to a second reactor.

The first section of the first reactor was heated to 80° C., the second section of the first reactor was heated to 180° C., and the second reactor was heated to 250° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H$_2$ were mixed and introduced to a preheater, in which a molar ratio of hexafluoropropylene to H$_2$ was 4:1 and a space velocity was 500 h$^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 5:

TABLE 5

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.1 | 0 | 37.8 | 62.0 | 0.2 |
| Second reactor (wt. %) | 71.1 | 28.5 | 0.1 | 0.2 | 0.1 |

EXAMPLE 6

200 mL of Pd/AlF$_3$ as a third catalyst (Pd accounts for 3 wt. %) was added to a third section of a first reactor, 300 mL of a second catalyst comprising 6 wt. % of chromium oxide, 90 wt. % of alumina, and 4 wt. % of zinc oxide was added to a second section of the first reactor, and 200 mL of Pd/Al$_2$O$_3$ as a first catalyst (Pd accounts for 1.5 wt. %) was added to a first section of the first reactor. 700 mL of a fourth catalyst comprising 63 wt. % of chromium oxide, 6 wt. % of indium oxide, and 31 wt. % of nickel oxide was added to a second reactor.

The first section of the first reactor was heated to 150° C., the second section of the first reactor was heated to 250° C., and the second reactor was heated to 400° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H$_2$ were mixed and introduced to a preheater, in which a molar ratio of hexafluoropropylene to $H_2$ was 2.1:1 and a space velocity was 300 $h^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 6:

TABLE 6

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.1 | 0.1 | 28.5 | 71.2 | 0.1 |
| Second reactor (wt. %) | 58.5 | 41.0 | 0.1 | 0.2 | 0.2 |

EXAMPLE 7

200 mL of Pd/AlF$_3$ as a third catalyst (Pd accounts for 0.5 wt. %) was added to a third section of a first reactor, 300 mL of a second catalyst comprising 10 wt. % of chromium oxide, 86 wt. % of alumina, and 4 wt. % of zinc oxide was added to a second section of the first reactor, and 200 mL of Pd/Al$_2$O$_3$ as a first catalyst (Pd accounts for 0.5 wt. %) was added to a first section of the first reactor. 700 mL of a fourth catalyst comprising 70 wt. % of chromium oxide, 4 wt. % of indium oxide, and 26 wt. % of nickel oxide was added to a second reactor.

The first section of the first reactor was heated to 100° C., the second section of the first reactor was heated to 200° C., and the second reactor was heated to 310° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and $H_2$ were mixed and introduced to a preheater, in which a molar ratio of hexafluoropropylene to $H_2$ was 2:1 and a space velocity was 500 $h^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 7:

TABLE 7

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.1 | 0 | 44.8 | 55 | 0.1 |
| Second reactor (wt. %) | 68.9 | 30.8 | 0.1 | 0.2 | 0 |

EXAMPLE 8

200 mL of Pd/C as a third catalyst (Pd accounts for 0.5 wt. %) was added to a third section of a first reactor, 300 mL of a second catalyst comprising 5 wt. % of chromium oxide, 90 wt. % of alumina, and 5 wt. % of zinc oxide was added to a second section of the first reactor, and 200 mL of Pd/Al$_2$O$_3$ as a first catalyst (Pd accounts for 0.3 wt. %) was added to a first section of the first reactor. 700 mL of a fourth catalyst comprising 80 wt. % of chromium oxide, 5 wt. % of indium oxide, and 15 wt. % of nickel oxide was added to a second reactor.

The first section of the first reactor was heated to 120° C., the second section of the first reactor was heated to 250° C., and the second reactor was heated to 330° C. When heating the first reactor and the second reactor, a heating rate was controlled at 1° C./min within a temperature range of between a normal temperature and 150° C., and the heating rate was 0.5° C./min when the temperature exceeds 150° C. After the heating, the first reactor and the second reactor were ventilated with nitrogen for drying for 2 hrs.

Thereafter, materials were fed for reaction. Hexafluoropropylene and H$_2$ were mixed and introduced to a preheater, in which a molar ratio of hexafluoropropylene to H$_2$ was 2.2:1 and a space velocity was 600 h$^{-1}$. The first mixture comprising: 1,1,1,2,3-pentafluoropropane, 1,1,1,2,3,3-hexafluoropropane, and HF was discharged from the outlet of the first reactor and entered the first distillation column. The 1,1,1,2,3,3-hexafluoropropane yielded at the top of the first distillation column was recycled to the lower part of the first section of the first reactor, and the second mixture yielded at the bottom of the first distillation column was introduced to the second reactor. Mixtures at outlets of the first reactor and the second reactor were respectively collected and analyzed by gas chromatography, and compositions of organic compounds were as follows in Table 8:

TABLE 8

| Components | 2,3,3,3-tetra-fluoropropene | 1,3,3,3-tetra-fluoropropene | 1,1,1,2,3,3-hexafluoro-propane | 1,1,1,2,3-pentafluoro-propane | Others |
|---|---|---|---|---|---|
| First reactor (wt. %) | 0.2 | 0 | 39.5 | 60.2 | 0.1 |
| Second reactor (wt. %) | 56.8 | 43.1 | 0 | 0 | 0.1 |

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing 2,3,3,3-tetrafluoropropene and 1,3,3,3-tetrafluoropropene, the method comprising:
   a) providing a first reactor comprising a first section, a second section, and a third section, and loading a first catalyst, a second catalyst, and a third catalyst respectively to the first section, the second section, and the third section of the first reactor; preheating hexafluoropropylene and hydrogen, and introducing the hexafluoropropylene and the hydrogen to the first section to yield 1,1,1,2,3,3-hexafluoropropane and unreacted hydrogen; introducing the 1,1,1,2,3,3-hexafluoropropane and the unreacted hydrogen into the second section to yield a product; introducing the product into the third section to yield a first mixture comprising: 1,1,1,2,3-pentafluoropropane, unreacted 1,1,1,2,3,3-hexafluoropropane, and hydrogen fluoride, wherein a molar ratio of the hexafluoropropylene to the hydrogen is between 2:1 and 5:1 and a space velocity of the hexafluoropropylene and the hydrogen is between 100 and 1000 h$^{-1}$, a reaction temperature in the first section is between 50 and 200° C., a reaction temperature in the second section is between 150 and 300° C., and a temperature in the third section is maintained by materials from the second section;
   b) introducing the first mixture obtained from a) to a first distillation column to yield distilled 1,1,1,2,3,3-hexafluoropropane at a top of the first distillation column and first distilled 1,1,1,2,3-pentafluoropropane and distilled hydrogen fluoride at a bottom of the first distillation column; recycling the distilled 1,1,1,2,3,3-hexafluoropropane to a lower part of the first section of the first reactor; introducing the first distilled 1,1,1,2,3-pentafluoropropane and the distilled hydrogen fluoride to a second reactor to allow the first distilled 1,1,1,2,3-pentafluoropropane to react with the distilled hydrogen fluoride in the presence of a fourth catalyst at a reaction temperature of between 200 and 450° C. to yield a second mixture comprising: 2,3,3,3-tetrafluoropropene, 1,3,3,3-tetrafluoropropene, unreacted hydrogen fluoride, and unreacted 1,1,1,2,3-pentafluoropropane;
   c) washing the second mixture obtained in b) using water and an alkali respectively to yield a treated second mixture, drying the treated second mixture to yield a third mixture comprising: dried 2,3,3,3-tetrafluoropropene, dried 1,3,3,3-tetrafluoropropene, and dried 1,1,1,2,3-pentafluoropropane; introducing the third mixture into a second distillation column to yield distilled 2,3,3,3-tetrafluoropropene and distilled 1,3,3,3-tetrafluoropropene at a top of the second distillation column and second distilled 1,1,1,2,3-pentafluoropropane at a bottom of the second distillation column; and recycling the second distilled 1,1,1,2,3-pentafluoropropane to the second reactor; and
   d) introducing the distilled 2,3,3,3-tetrafluoropropene and the distilled 1,3,3,3-tetrafluoropropene obtained from c) into a third distillation column to yield final 2,3,3,3-tetrafluoropropene at a top of the third distillation column and final 1,3,3,3-tetrafluoropropene at a bottom of the third distillation column;
   wherein:
   in a),
      the first catalyst is Pd/Al$_2$O$_3$, and Pd accounts for between 0.3 and 3 wt. % of the total amount of the first catalyst;
      the second catalyst comprises: chromium oxide accounting for between 5 and 10 wt. % of the total amount of the second catalyst, alumina accounting for between 80 and 90 wt. % of the total amount of the second catalyst, and zinc oxide accounting for between 3 and 10 wt. % of the total amount of the second catalyst; and the third catalyst is Pd/AlF$_3$ or Pd/C, and Pd accounts for between 0.3 and 3 wt. % of the total amount of the third catalyst; and in b), the fourth catalyst comprises: chromium oxide accounting for between 60 and 80 wt. % of the total amount of the fourth catalyst, indium oxide accounting for between 4 and 10 wt. % of the total amount of the fourth catalyst, and nickel oxide accounting for between 10 and 35 wt. % of the total amount of the fourth catalyst.

2. The method of claim 1, wherein a molar ratio of the hydrogen to the hexafluoropropylene in a) is between 2:1 and 2.5:1; the space velocity of the hexafluoropropylene and the hydrogen is between 200 and 800 h$^{-1}$; the reaction temperature in the first section is between 55 and 150° C., and the reaction temperature in the second section is between 180 and 250° C.

3. The method of claim 1, wherein the reaction temperature of the second reactor in b) is between 250 and 400° C.

* * * * *